(12) United States Patent (10) Patent No.: US 7,929,742 B2
Maltz (45) Date of Patent: Apr. 19, 2011

(54) METHOD AND SYSTEM FOR COMPUTED TOMOGRAPHIC IMAGING

(75) Inventor: Jonathan Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 817 days.

(21) Appl. No.: 11/904,910

(22) Filed: Sep. 28, 2007

(65) Prior Publication Data

US 2009/0087055 A1 Apr. 2, 2009

(51) Int. Cl.
*G06K 9/00* (2006.01)
*A61B 6/00* (2006.01)

(52) U.S. Cl. .......................................... 382/128; 378/4
(58) Field of Classification Search .......... 382/128–132; 378/4–27

See application file for complete search history.

(56) References Cited

U.S. PATENT DOCUMENTS

| | | | | |
|---|---|---|---|---|
| 4,305,127 A | * | 12/1981 | Heuscher | 600/425 |
| 4,482,958 A | * | 11/1984 | Nakayama et al. | 378/14 |
| 5,493,593 A | * | 2/1996 | Muller et al. | 378/19 |
| 5,740,224 A | * | 4/1998 | Muller et al. | 378/11 |
| 5,951,475 A | * | 9/1999 | Gueziec et al. | 600/425 |
| 5,953,388 A | * | 9/1999 | Walnut et al. | 378/4 |
| 6,075,836 A | * | 6/2000 | Ning | 378/98.12 |
| 6,219,403 B1 | * | 4/2001 | Nishihara | 378/65 |
| 6,246,742 B1 | * | 6/2001 | Besson et al. | 378/8 |
| 6,298,110 B1 | * | 10/2001 | Ning | 378/4 |
| 6,426,988 B2 | * | 7/2002 | Yamada et al. | 378/4 |
| 6,539,103 B1 | * | 3/2003 | Panin et al. | 382/131 |
| 6,907,100 B2 | * | 6/2005 | Taguchi | 378/4 |
| 7,251,307 B2 | * | 7/2007 | Chen | 378/4 |
| 7,324,660 B2 | * | 1/2008 | Oosawa | 382/100 |
| 2006/0109952 A1 | * | 5/2006 | Chen | 378/4 |
| 2009/0046830 A1 | * | 2/2009 | Yin | 378/9 |

* cited by examiner

*Primary Examiner* — Manav Seth

(57) ABSTRACT

The present invention is a method and system for computed tomography imaging. The system for computed tomography imaging may comprise: a) an x-ray source; b) an x-ray detector; and c) a processing unit, wherein the processing unit is configured to carry out the steps: i) obtaining CT projections of an object, the projections comprising at least one truncated projection; ii) calculating material-equivalent thickness (MET) values for the truncated projection; iii) establishing parameterized point-pairs separated in distance by the MET values; iv) fitting the parameterized point-pairs to a parameterized curve or to a set of curves according to a set of constraints on spatial relationships between the point-pairs; v) completing the truncated projections; and vi) reconstructing a CT image from non-truncated projections and the completed truncated projections.

24 Claims, 20 Drawing Sheets

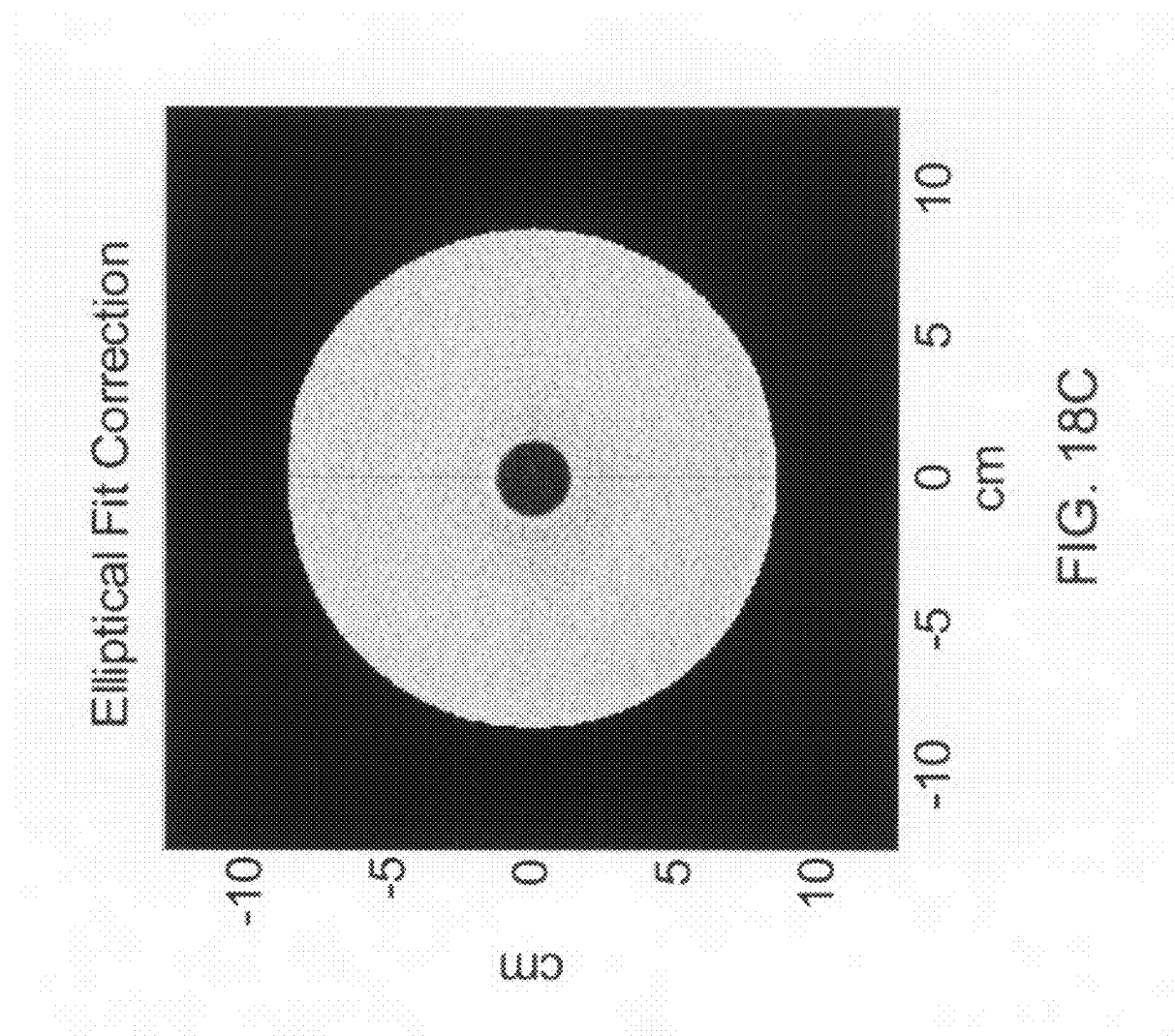

METHOD AND SYSTEM FOR COMPUTED TOMOGRAPHIC IMAGING

BACKGROUND

Large patient anatomies and limited imaging field-of-view (FOV) may lead to truncation of computed tomography (CT) projections. Truncation introduces serious artifacts into reconstructed images, including central cupping and bright external rings. FOV may be increased using laterally offset detectors, but this requires sophisticated imaging hardware and full angular scanning. When linear particle accelerators (LINACs) equipped with mini-multileaf collimators (MLCs) are used for mega-voltage cone beam CT imaging, truncation is inevitable.

Due to limited flat-panel detector size, constraints of mechanical motion, and large patient sizes, projection truncation artifacts in cone beam CT (CBCT) present a unique challenge for applications in multiple clinical domains. Even with the employment of brute force approaches, such as the use of lateral offset detectors and full angular scanning, practical trade-offs exist with respect to acquisition time and computational burden. Furthermore, in more specific domains, such as radiotherapy (RT), there exist compromises when mechanical collimation is dictated by the interventional system, and such constraints are of serious clinical importance. An example is megavoltage CBCT for precise stereotactic RT, where image guidance is provided through a tertiary rectangular mini-MLC placed close to a patient. Such an arrangement yields an optimal geometry for the production of a small beam aperture and tight penumbra.

It is often difficult to reconstruct an image of an object from truncated projections. However, various techniques have been suggested to minimize the effect of truncation artifacts and generate approximate solutions. Typical solutions include: 1) modifying projections to conform to a consistency condition derived from non-truncated projections or 2) smoothing truncated edges without consideration of any consistency conditions.

A typical example of the first type of solutions includes a methodology where projections are rebinned into parallel projections. Such a method assumes that at least one of the projections is not truncated. The sum of all rays along the untruncated parallel projection is calculated. All truncated projections are then extended with projections of water cylinders at the truncated edges so that total attenuation of a modified projection matches this sum. Another example of the first type of solutions uses prior CT information to complete CBCT data. There are also several solutions available for exact region-of-interest (ROI) reconstruction in truncated data conditions, using techniques such as backprojection filtration. Such solutions may be computationally intensive and/or difficult to employ in practice. They may also be restricted in terms of the sampling geometries for which they are appropriate.

Solutions in the second category involve techniques such as extrapolation methods based on fitting elliptical boundary segments or using symmetric mirroring and smoothing of the projection data beyond the truncated region. While these methods are arguably more practical than the consistency-condition solutions, the results tend to be imprecise.

SUMMARY OF THE INVENTION

Accordingly, a system and method for completing truncated CT projections based on measurements of radiological path lengths of the object are presented. We define the material-equivalent thickness (MET) as the thickness of a material having a composition analogous to that of the imaged object. The MET along a specific ray traversing the object is equal to the physical thickness of the analogous material that produces the same attenuation of the primary beam as the imaged object along that ray.

A method for computed tomography imaging may comprise: a) obtaining CT projections of an object, the projections comprising at least one truncated projection; b) calculating material-equivalent thickness (MET) values for the truncated projection; c) establishing parameterized point-pairs, each point-pair being separated in space by a distance equal to the MET value and each point-pair lying along the direction of the original ray from which the MET value was derived, d) fitting the parameterized point-pairs to a parameterized curve or to a set of contours, under a set of constraints on the spatial relationships between point-pairs; e) completing the truncated projection; and f) reconstructing a CT image from non-truncated projections and the completed truncated projections.

A system for computed tomography imaging may comprise: a) an x-ray source; b) an x-ray detector; and c) a processing unit, wherein the processing unit is configured to carry out the steps: i) obtaining CT projections of an object, the projections comprising at least one truncated projection; ii) calculating material-equivalent thickness (MET) values for the truncated projection; iii) establishing parameterized point-pairs from the MET values; iv) fitting the parameterized point-pairs to a parameterized curve or to a set of contours, under a set of constraints on the spatial relationships between point-pairs; v) completing the truncated projection; and vi) reconstructing a CT image from non-truncated projections and the completed truncated projections.

It is to be understood that both the foregoing general description and the following detailed description are exemplary and explanatory only and are not restrictive of the claims. The accompanying drawings, which are incorporated in and constitute a part of the specification and merely serve to explain the principles of the description.

BRIEF DESCRIPTION OF THE DRAWINGS

The numerous objects and advantages of the present invention may be better understood by those skilled in the art by reference to the accompanying figures in which:

FIG. 18C depicts a CT reconstruction of the water phantom obtained using a cone beam CT imaging system where the truncated projections have been corrected using the present algorithm and the sampling geometry of FIG. 16;

DETAILED DESCRIPTION

Figure 1:
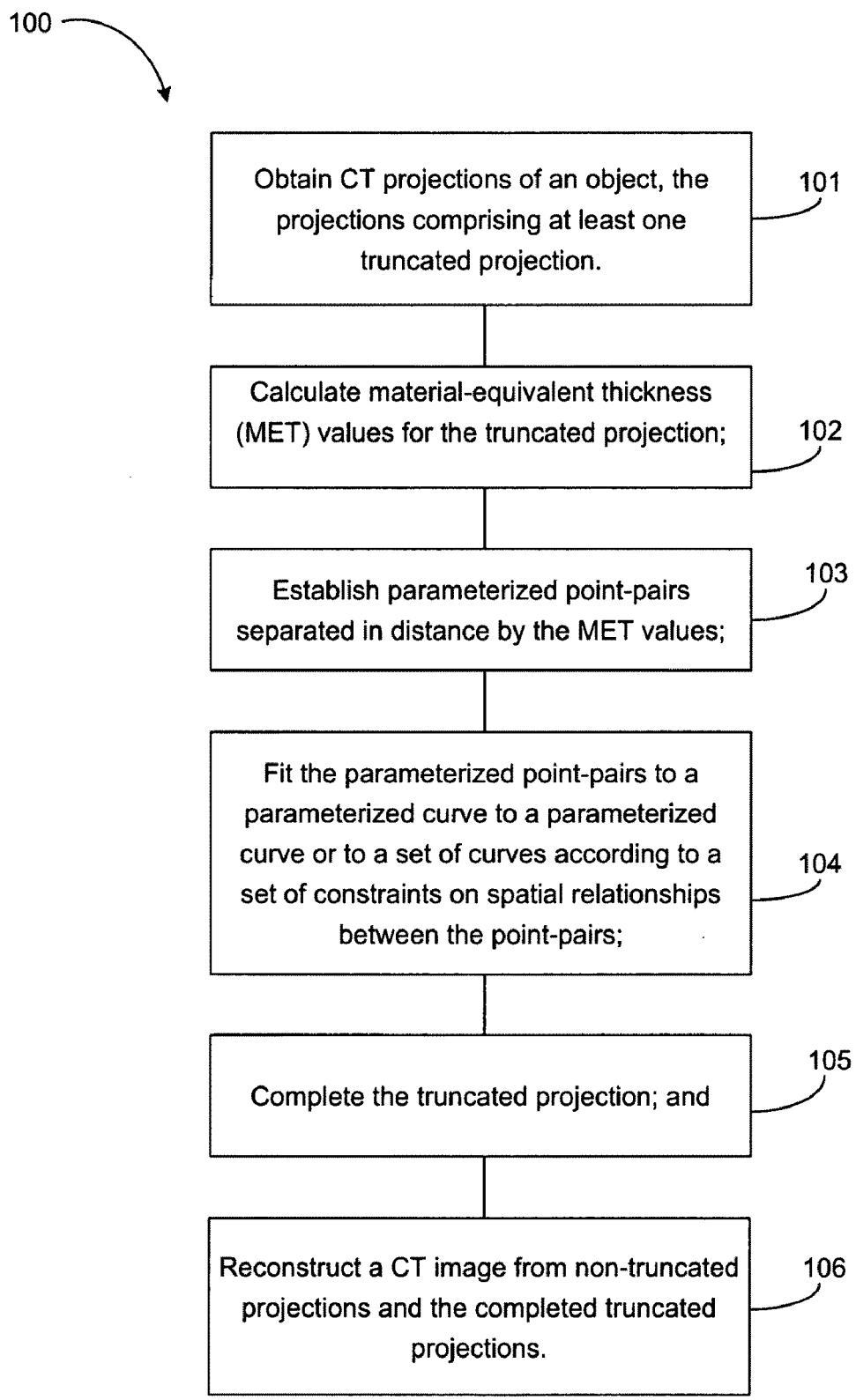
FIG. 1 depicts a process flowchart detailing a method for CT imaging.

The following description is presented to enable a person skilled in the art to make and use the present invention. Various modifications to the description will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, are not intended to limit the scope of the present teachings. Skilled artisans will recognize the examples provided herein have many useful alternatives and fall within the scope of the present teachings.

The present invention is directed to a system and method for completion of truncated CT projections by calculating a material-equivalent thickness (MET) for the truncated CT projections. Additional details of the invention are provided in the examples illustrated in the accompanying drawings.

Referring to FIG. 1, a process flow diagram for a method for CT imaging 100 is shown. A plurality of CT projections of an object may be obtained at step 101. The projections may comprise at least one truncated projection.

Figure 2:
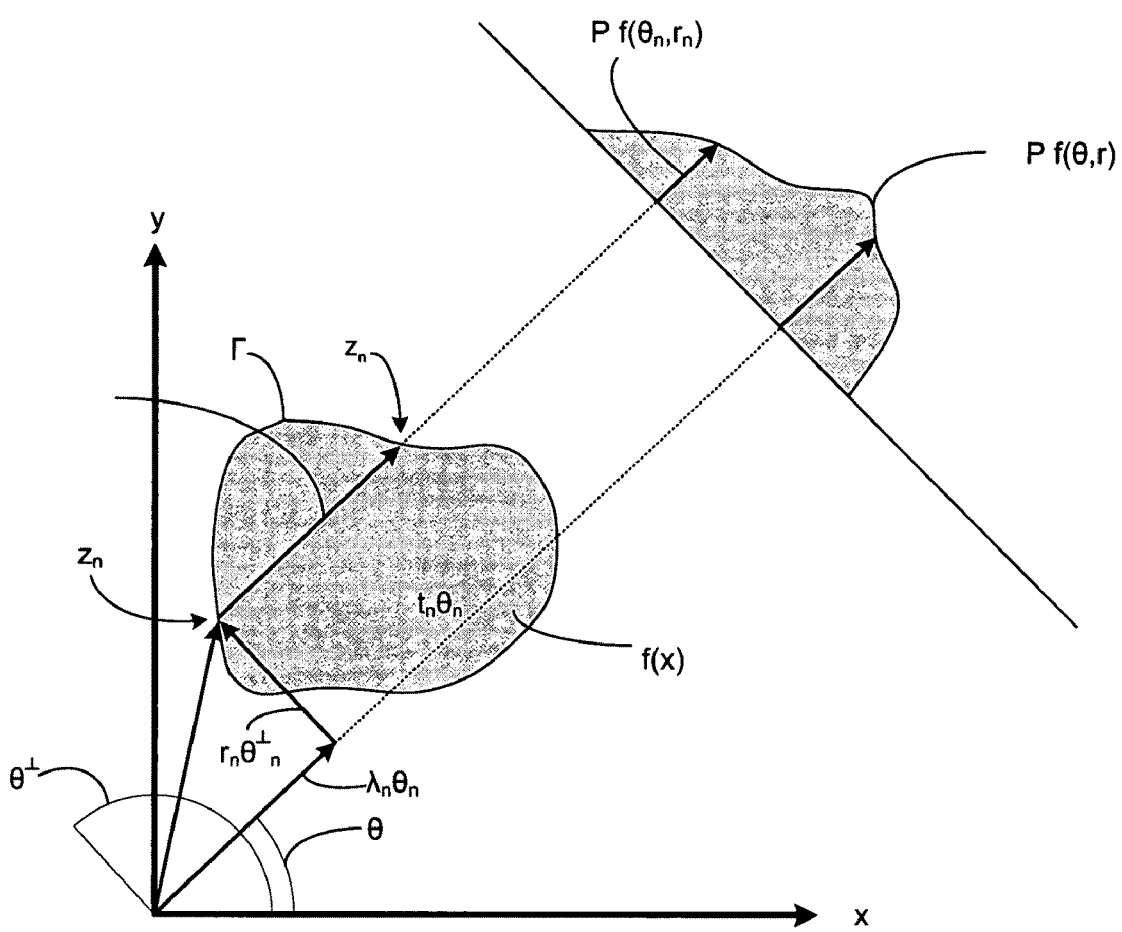
FIG. 2 depicts coordinate conventions for the x-ray transform and point-pair parameterization.

Referring to FIG. 2, a diagram illustrating the coordinate conventions for the x-ray transform and point-pair parameterization is presented. A direction vector $\theta$ may be oriented along a given ray path having a relative angle defined as $\theta$. A radial coordinate r may be oriented perpendicular to the ray at an angle defined as $\theta^\perp$ along direction vector $\theta^\perp$. An external boundary $\Gamma$ encloses the function f(x) (representing the object to be imaged).

The x-ray transform of an arbitrary distribution f(x), s ∈ $\Re^3$, is given by:

$$P f(\theta, r) = \int_{-\infty}^{\infty} f(x + \kappa \theta) d\kappa \quad \text{(Equation 1)}$$

where P f($\theta$, r) is the line integral for a ray passing through the object defined by f(x).

Let P f($\theta_n$, $r_n$) represent the line integral for a specific ray along vector $\theta$ at radial position $r_n$. Let $z_n$ and $z_n'$ represent the two intersection points between the ray and the boundary $\Gamma$: Then:

$$z_n = r_n \theta_n^\perp + \lambda_n \theta_n \quad \text{(Equation 2)}$$

$$z_n' = z_n + t_n \theta_n \quad \text{(Equation 3)}$$

where $t_n$ is the distance (thickness) between the two intersection points $z_n$ and $z'_n$ along the ray and $\lambda_n$ is the distance from the x-ray source to a given point on the boundary surface of the imaged object.

In order to correct for truncated portions of the object defined by f(x), the $t_n$ value may be estimated as a material-equivalent thickness (MET) determined from the projections (having been corrected for scatter and beam hardening). A MET for a particular ray traversing an object is defined as the distance in a material having a composition analogous to that of the imaged object that the same ray would travel in order to be attenuated by the same amount it is attenuated on its path through the object.

Referring again to FIG. 1, MET values for the truncated projection may be calculated at step 102. The MET may be calculated by:

1) Fitting a primary transmission model for propagation through a material analogous to the characteristic composition of the object to be imaged to the resultant imaging beam.

This can be done given knowledge of the beam spectrum, the attenuation properties of a material having a composition analogous to the characteristic composition of the object to be imaged, and the energy-dependent response of the detector.

In medical applications, the analogous material may be water. However, the present description fully contemplates the use of any material which may have compositions similar to those of an object to be imaged as the basis for computing a MET.

A suitable model with demonstrated accuracy in modeling polychromatic x-ray beams over a wide energy range is a beam transmission fraction of the form:

$$\tau(t) = \frac{I(t)}{I(0)} = e^{-\frac{\alpha t}{1 + \beta t}} \quad \text{(Equation 4)}$$

where $\tau(t)$ is the beam transmission fraction, I(0) represents incident beam intensity (as measured by the specific detector) and I(t) denotes measured beam intensity after traversing a distance t in the analogous material for which METs are calculated. Parameters $\alpha$ and $\beta$ are fundamental attenuation properties of the incident beam. These parameters may be determined by fitting the above model to a curve relating primary beam transmission to the thickness of the analogous material transversed by the beam. This curve can be determined using physical measurements obtained by propagating a pencil beam through various thicknesses of the analogous material.

Alternatively, when a beam spectrum $\phi$(E) and energy-dependent detector response function $\psi$(E) are known, the curve is more easily derived by analytical computation, given the energy-dependent attenuation coefficient of an analogous material μ(E):

$$\tau(t) = \frac{\int_0^\infty \phi(E) \cdot e^{-\mu(E)t} \cdot \psi(E) dE}{\int_0^\infty \phi(E) dE} \quad \text{(Equation 3)}$$

where E represents photon or particle energy.

2) Converting the x-ray transform values into METs.

As previously stated, with respect to FIG. 2, the x-ray transform of an arbitrary distribution f(x), where $x \in \Re^3_r$ is be given by:

$$P f(\theta, r) = \int_{-\infty}^\infty f(x + \kappa\theta) d\kappa \quad \text{(Equation 1)}$$

The following Equation may be solved to compute a MET:

$$t_n = \underset{t}{\operatorname{argmin}} \left[ \frac{I_n(\theta_n, r_n)}{I_0} - \tau(t) \right]^2 \quad \text{(Equation 5)}$$

where $I_n(\theta_n, r_n)$ is a raw-data value beam-intensity (as observed by a detector) corresponding to $P f(\theta_n, r_n)$. $I_0$ is a raw-data value beam-intensity (as observed by a detector) when no object is present in the field of view (often termed the normalization scan, air image or flood field image).

Accurate MET values may also be derived from cone beam computed tomography (CBCT) projections using a convolution/superposition algorithm obtained using both kV and MV beams such as those presented in "Unified algorithm for kV and MV scatter and beam-hardening correction using the convolution-superposition method". Maltz et al, *Medical Physics*, 33(6):2280-2280, (2006), incorporated herein by reference in its entirety.

It should be noted that the presence of anomalous portions of an object (i.e. those with dramatically higher or lower mass densities) may pose problems in determining MET values.

For example, in medical applications utilizing water-equivalent thicknesses (WET) as the particular MET for correcting truncated portions of a human anatomy, metal prostheses may pose a problem in that true thickness values may be overestimated by WET values when kV beams are employed. Such conditions may be ameliorated using existing methods of sinogram modification. By performing a preliminary reconstruction of the modified sinogram, it should be possible to apply corrections to the thickness estimates. Sampled rays associated with unrealistically large thickness estimates (such as those that traverse high atomic-number materials), may be replaced with other ray samples that yield reasonable thickness estimates.

Similarly, imaging of a thorax containing a large proportion of air volume may result in WET calculations which greatly underestimate true thickness of the imaged object. This problem may be addressed by performing an initial reconstruction, substituting the air volume for water, and then determining the truncation correction from the recalculated projections. The correction may then be applied to the original projections which may then be reconstructed.

Referring again to FIG. 1, intersection points-pairs (such as $[z_n, z'_n]$ of FIG. 2), may be parameterized at step 103. Referring again to FIG. 2, given a calculated MET, $t_n$ for a ray along $\theta_n$ at $r=r_n$ and a correct value of $\lambda_n$, it may be possible to parameterize a point-pair $[z_n, z'_n]$ separated by a distance $t_n$ where each point may be located on the boundary of $f(x \pm \kappa_n \theta_n)$ where $\kappa_n$ represents an unknown translation. Consideration of N rays at unique values of $\theta_n$ and $r_n$ increases to N the number of MET samples $t_n$ available but also introduces N unknowns ($\lambda_1$ to $\lambda_N$).

In order to account for these unknowns it may be assumed that $\Gamma$ may be approximated by a parameterized curve, or as a set of contours that constrain the point-pairs in space. Referring to FIG. 1, the parameterized point-pairs may be fit a parameterized curve at step 104.

Figure 3:
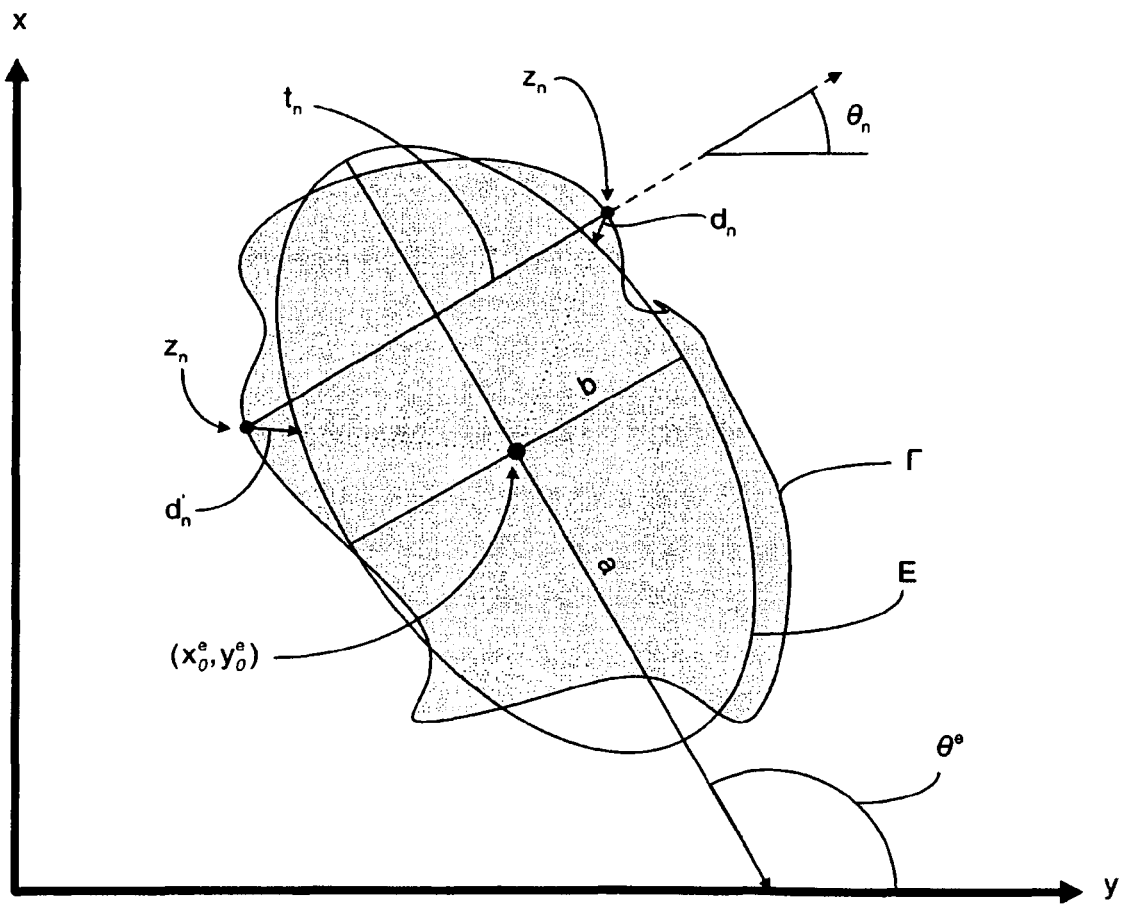
FIG. 3 depicts a metric correlating the goodness-of-fit between an elliptical boundary and an imaged object boundary.

In medical CT imaging applications, it may be assumed that $\Gamma$ may be approximated by an ellipse representing large body parts, as will be presented below. However, a person of ordinary skill in the art will readily recognize that any parameterized curve in $\Re^2$or $\Re^3$may be used. (Alternatively, the point pairs can be fit to a set of contours, under a set of spatial constraints on the relationship between point-pairs in space. For example, the distance between corresponding point-pairs on two rays that are closest to each other may be minimized over all pairs of rays.) Referring to FIG. 3, in order to find a solution for an elliptical boundary $\Gamma_\Theta$ closely approximating the full-view image of an object boundary $\Gamma$, a metric correlating the goodness-of-fit between boundary points $z_n=[x_n, y_n]^T$ of the object boundary $\Gamma$ and the estimated elliptical boundary $\Gamma_e$ may be defined. The squared elliptical norm ($d^2$) of a vector d that joins a boundary point $z_n$ and $\Gamma_e$ (and that intersects the centroid of the ellipse $[x_0^e, y_0^e]$) may be used to approximate goodness-of-fit according to:

$$d^2(z_n, a, b, \theta^\theta, x_0^\theta, y_0^\theta) = \\ 1 - \frac{[u_n - u_0^\theta]^2}{a^2} - \frac{[v_n - v_0^\theta]^2}{b^2} \quad \text{(Equation 6)}$$

where: (Equation 7A and 7B)

$$\begin{bmatrix} u_n \\ v_n \end{bmatrix} = R \begin{bmatrix} x_n \\ y_n \end{bmatrix} \quad \begin{bmatrix} u_0^\theta \\ v_0^\theta \end{bmatrix} = R \begin{bmatrix} x_0^\theta \\ y_0^\theta \end{bmatrix}$$

and:

$$R = \begin{bmatrix} \cos(\theta^\theta) & \sin(\theta^\theta) \\ -\sin(\theta^\theta) & \cos(\theta^\theta) \end{bmatrix} \quad \text{(Equation 8)}$$

An ellipse may be parameterized according to semi-major axis a, semi-minor axis b, semi-major axis orientation $\theta^e$ and centroid $(x_0^e, y_0^e)$. A vector $s=[a \ b \ \theta^e \ x_0^e \ y_0^e]^T$ may be defined which contains the unknown ellipse parameters. Similarly, a vector $\lambda=[\lambda_1 \ \lambda_2 \ldots \lambda_n]^T$ may comprise vectors $\lambda_n$ representing distance and angular relationships between the x-ray source and a parameterized point $z_n=[x_n, y_n]^T$ of the object boundary $\Gamma$.

To find the single ellipse that minimizes the sum of all squared distances $d^2$ between its boundary and all of the parameterized point-pairs $[z_n, z'_n]$, the following equation may be solved:

$$\min_{\lambda, s} \sum_1^N d^2(\lambda_n, s) \quad \text{(Equation 9)}$$

This minimization optimization yields an ellipse parameter vector s.

Referring to FIG. 1, the truncated projections may be completed at step 105. To complete the projection data reconstruction, projection values which are missing due to a limited FOV may be calculated from the parameterized curve. Referring to FIG. 3, where the parameterized curve is an ellipse, the truncated projections values may be calculated using the formula:

$$Pf(\theta, r) = \frac{2a_n b_n [a^2 \cos(\theta + \theta^\beta) + b^2 \sin(\theta + \theta^\beta)]^{-1} \times}{\sqrt{a^2 \cos(\theta + \theta^\beta) b^2 \sin(\theta + \theta^\beta) - [r - x_0^\beta \cos(\theta) - y_0^\beta \sin(\theta)]^2}} \quad \text{(Equation 10)}$$

which gives the line integrals through an analogous material-filled ellipse in the extrapolated region outside the FOV. Alternately, when an analytical expression of the line integrals of the boundary shape is not available, a digital "phantom" representation of the ellipse can be generated and ray sums can be calculated numerically from this phantom.

Referring to FIG. 1, the completed projections may then be used in concert with the original non-truncated projections to reconstruct a CT image at step 106.

Once all projections are completed, they may be passed to a reconstruction algorithm as intensity projections (in which case a logarithmic transform may be applied before reconstruction ensures) or as images of MET (in which case, no logarithmic transform is needed). In the latter case, the resultant projections may be corrected not only for truncation, but also for beam-hardening and scatter (as a consequence of their earlier conversion to MET maps).

Similarly, the steps of the method 100 may be implemented as computer readable instructions which may be stored on a computer readable medium. These computer readable instructions may comprise firmware or software and may be executed by a processing device such as an ASIC or a microprocessor.

Figure 4:
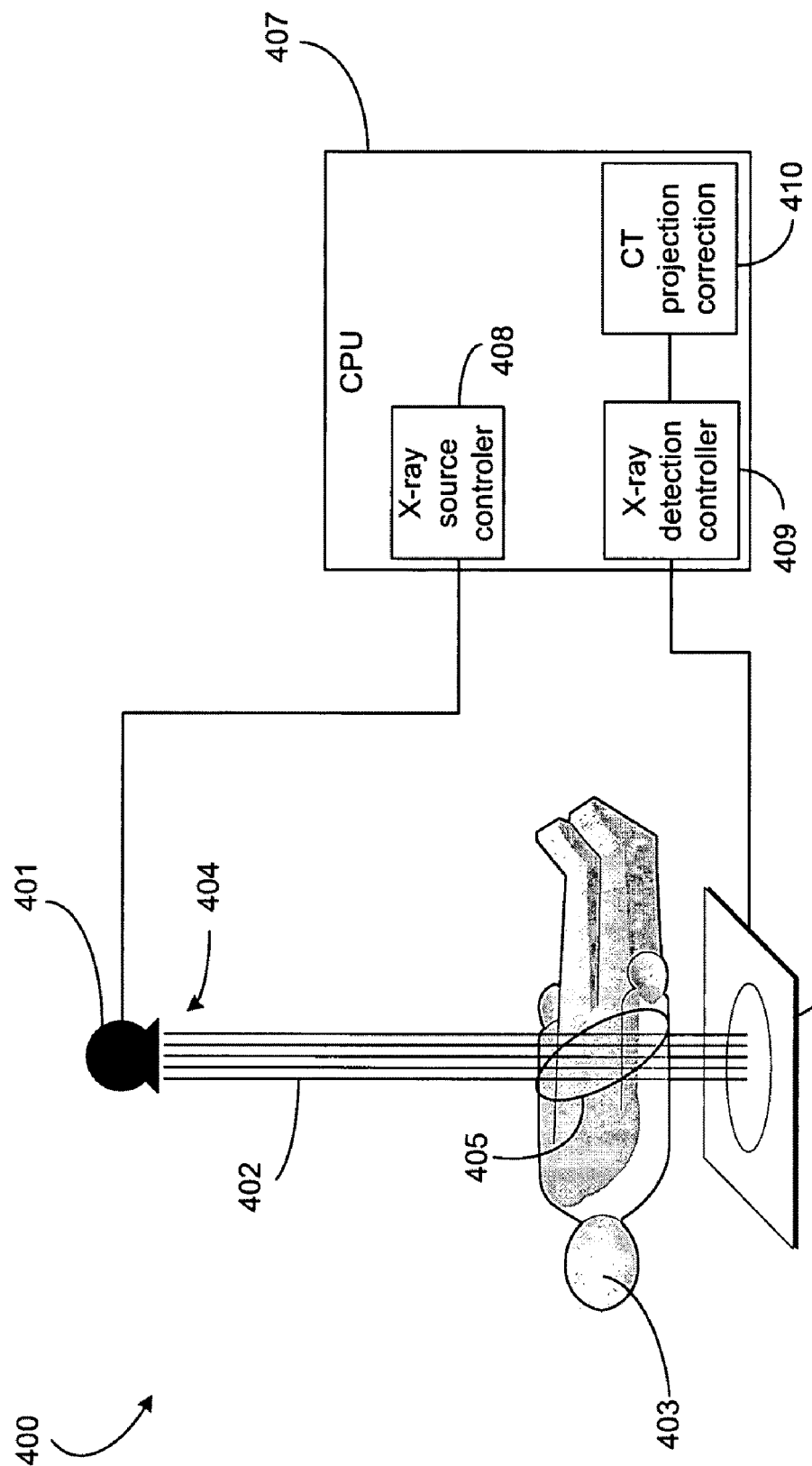
FIG. 4 depicts a CT imaging system.

Referring to FIG. 4, a system 400 for CT imaging is depicted. The system may comprise an x-ray source 401 configured to direct x-rays 402 towards an object to be imaged 403. The x-ray source 401 may lack a sufficient field of view 404 to adequately image an entire cross section 405 of the object to be imaged 403, thereby resulting in truncated x-ray projections. An x-ray detector 406 may be disposed in a position where the object to be imaged 403 may be aligned between the x-ray source 401 and the detector 406.

The system may further comprise a processing unit 407 including an x-ray control system 408, an x-ray detection system 409, and a CT projection correction system 410. The x-ray control system 408 may comprise application specific integrated circuitry (ASIC), firmware, or software configured run on a microprocessor to control the firing of the x-ray source 401. The x-ray detection system 409 may comprise ASIC, firmware or software configured to sample signals from the x-ray detector 406. The CT projection correction system 410 may comprise ASIC, firmware or software configured to receive x-ray projections from the x-ray detection system and correct those x-ray projections which may be truncated due to the limited field of view 404 of the x-ray source 401.

EXAMPLE

Referring to FIGS. 5-15, an example of the employment of the above described system and method is presented.

Figure 5:
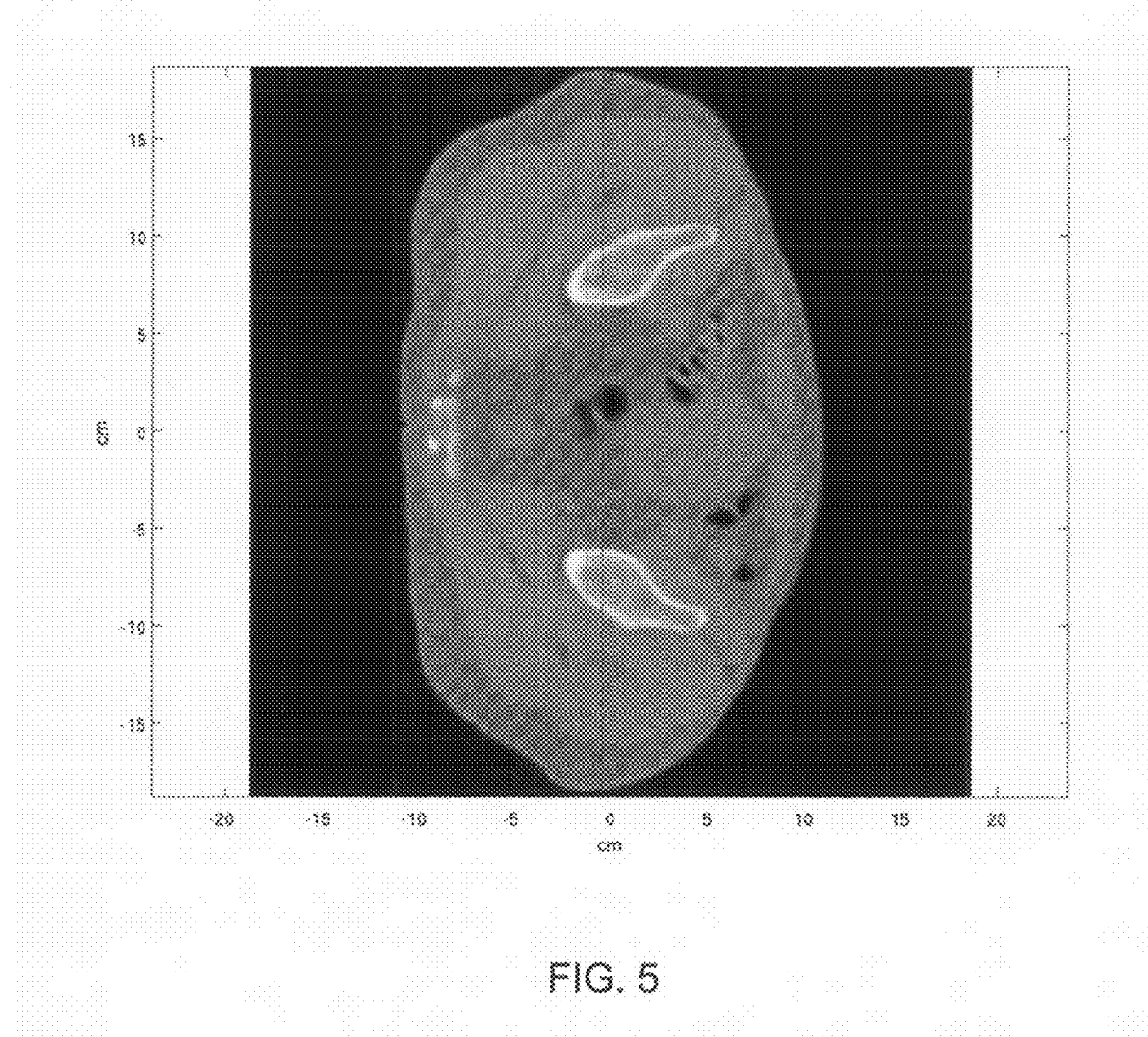
FIG. 5 depicts a reconstructed slice of the CT of a patient abdomen obtained from untruncated projections.
Figure 6:
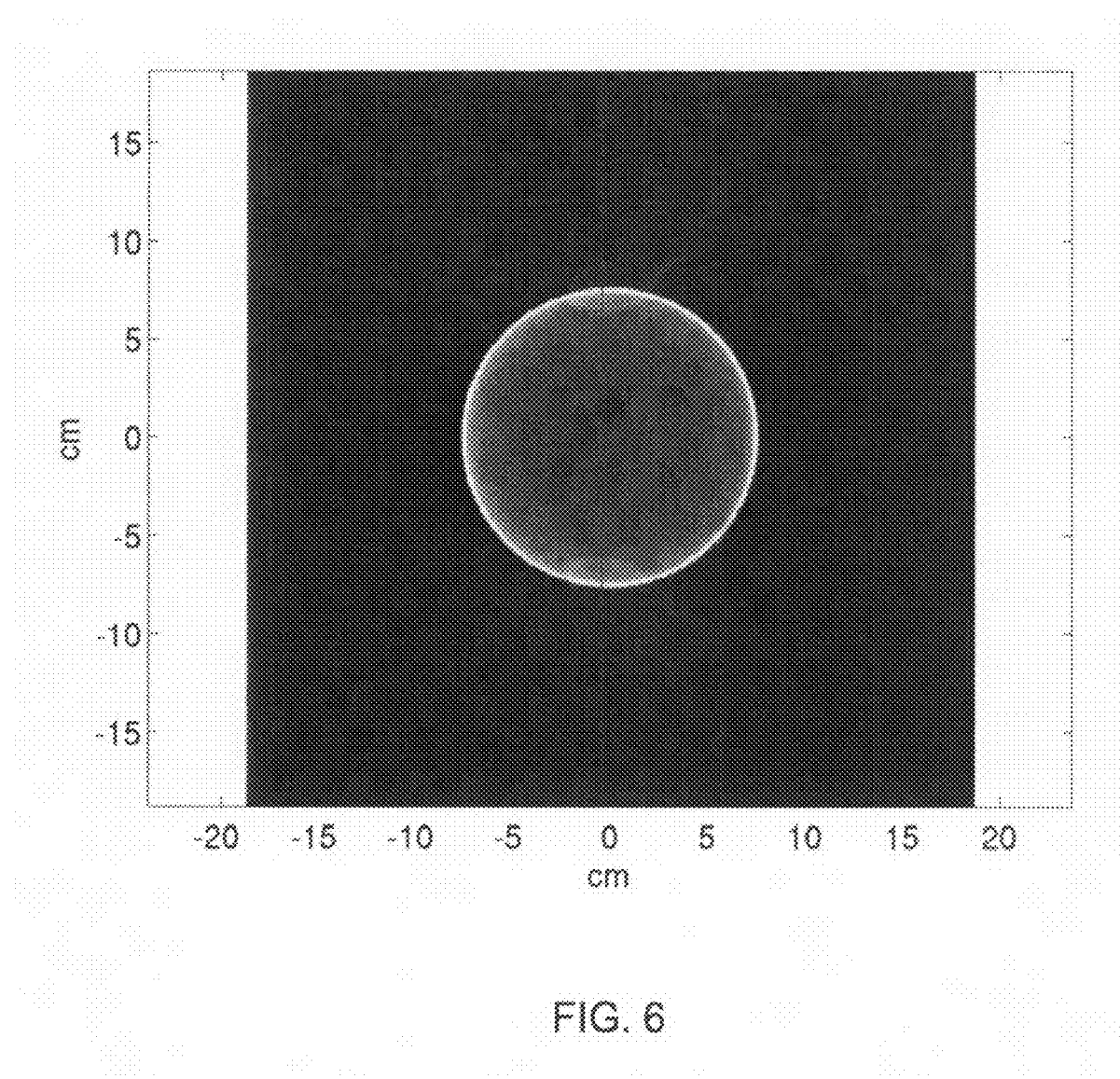
FIG. 6 depicts a reconstructed slice of the CT of a patient abdomen obtained from truncated projections.
Figure 7:
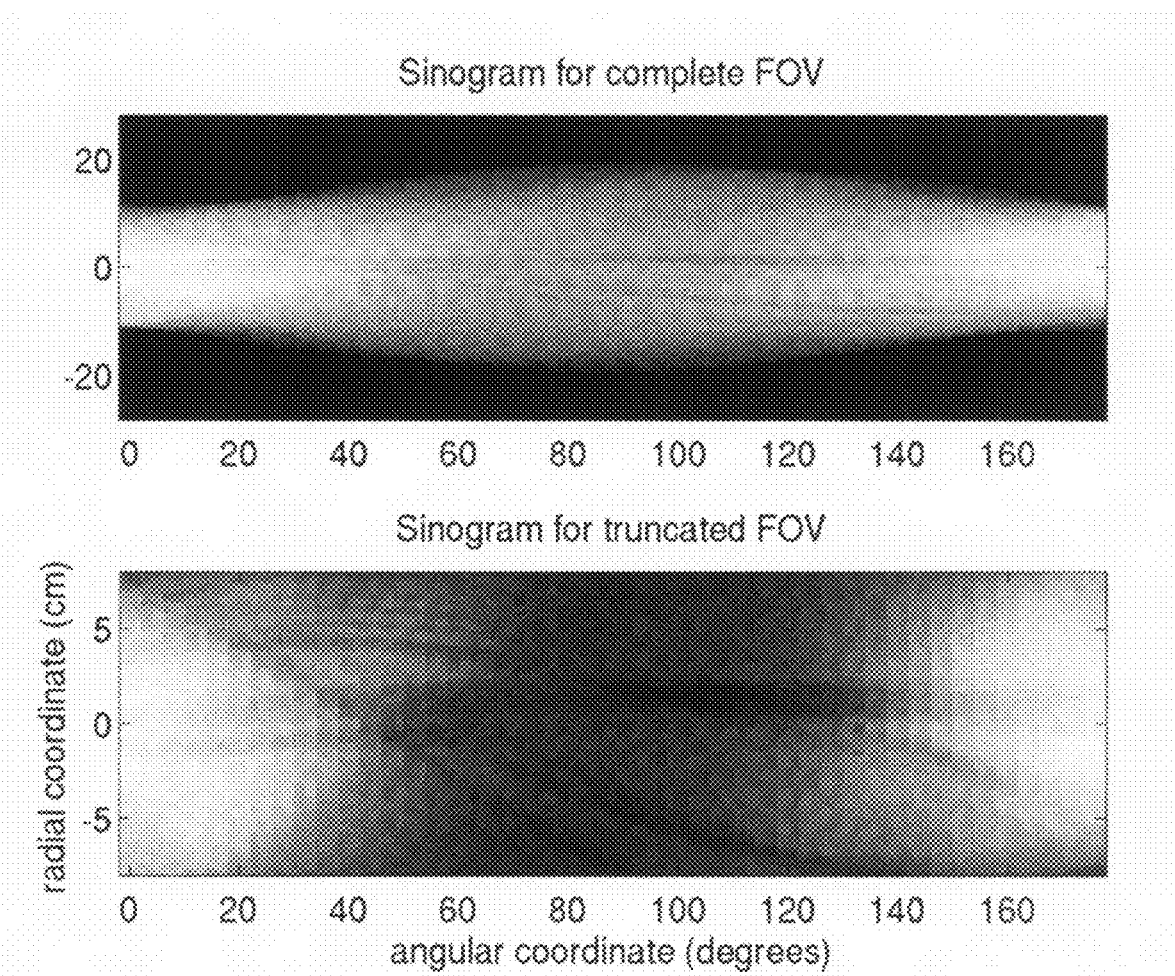
FIG. 7 depicts sinograms for complete and truncated projections obtained from CT imaging of a patient abdomen.

Referring to FIGS. 5 and 6, a complete CT image of a patient abdomen and a truncated CT image of patent abdomen are shown where a common axis is shown as a dotted line. Assuming that the imaging system has an actual FOV radius of 8 cm, FIG. 7 illustrates the sinograms for the complete and truncated sets. In order to perform boundary estimation, three rays are sampled at r=−6.1 cm, r=0 cm and r=4 cm (as the FOV limit is at |r|=8 cm). Rays were sampled for 45 angular projections separated by 4 degrees. As such, the optimization was performed over the 45×3-element λ vector and the 5-element ellipse parameter vector s.

Optimization Equation 9 was solved using a conjugate gradient (CG) algorithm. The CG algorithm may be cold-started with λ=0 and s=[0.01, 0.01, 0, 0, 0]$^T$. The analysis was also repeated with the original CT image offset 14 cm in the x-direction and 9 cm in the y-direction to ensure robustness when a patient is not centered in the FOV.

Figure 8:
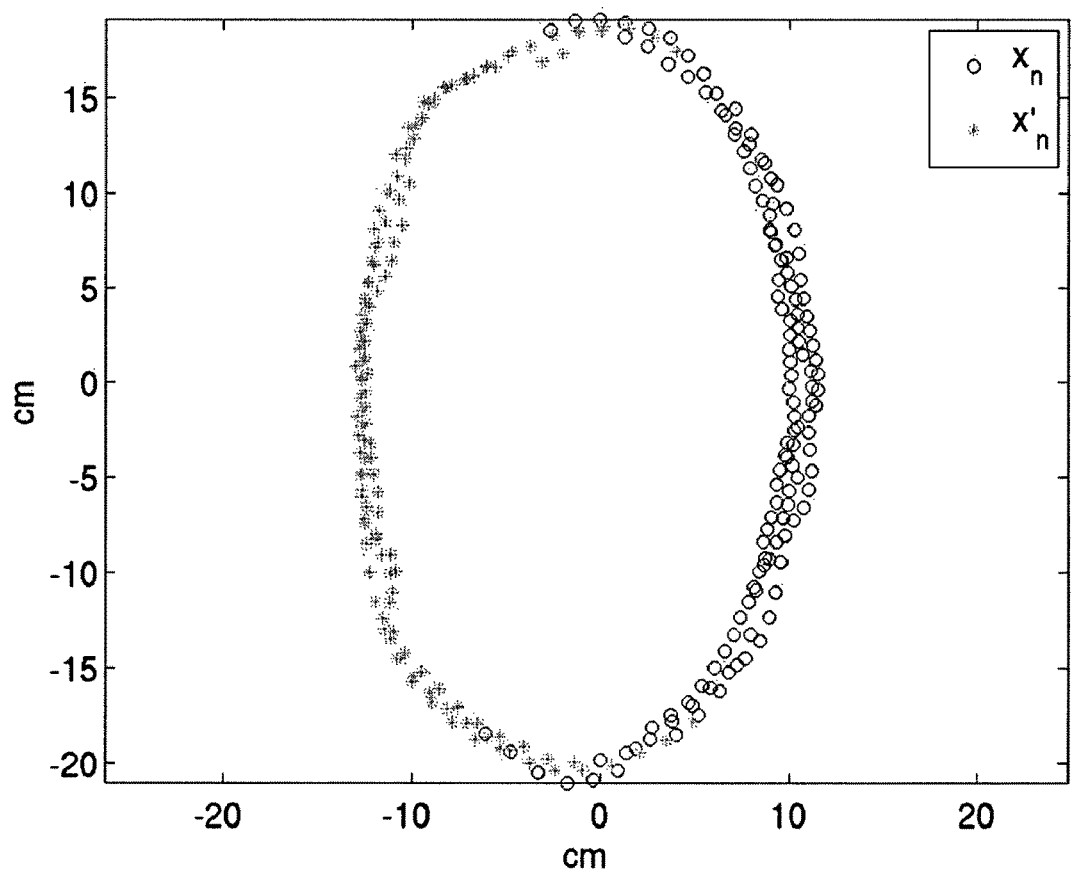
FIG. 8 depicts a plot of a distribution of intersection point-pairs.
Figure 9:
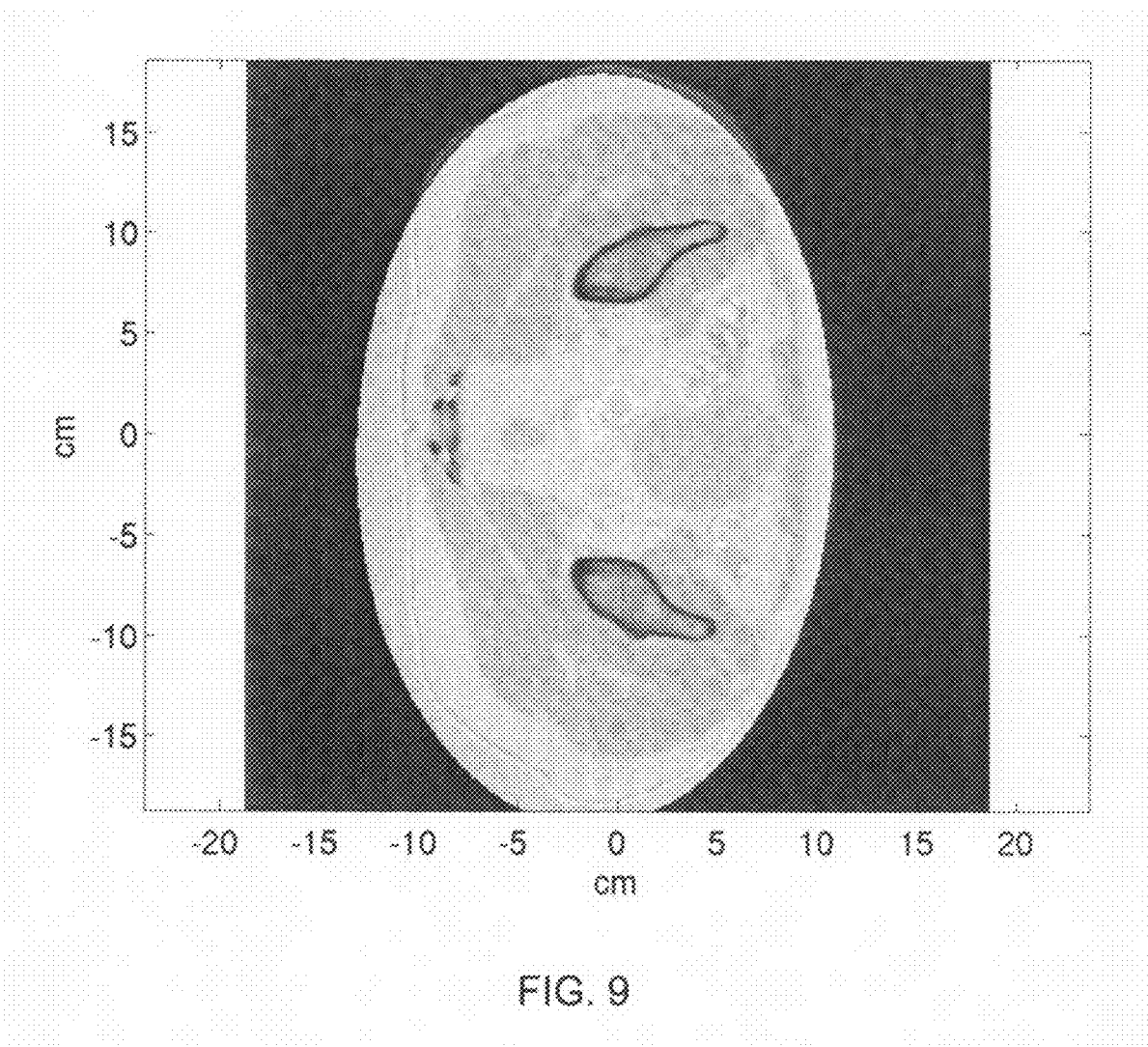
FIG. 9 shows a slice of a CT dataset obtained from complete projections superimposed on a solution ellipse.

Referring to FIG. 8, a plot of the distribution of intersection point-pairs $(z_n, z'_n)$ after optimization while FIG. 9 shows the original CT dataset superimposed on a solution ellipse having parameters s following optimization.

For comparative purposes an empirical extrapolation of the truncated data using a symmetric mirroring and smoothing approach as presented in "*Efficient correction for CT image artivacts caused by objects extending outside the scan field of view*"; Ohnesorge et. al.; *Medical Physics*, 27(1):39-46, 2000 (incorporated herein by reference) is also presented. In such an approach, for each projection, projection data within $w_1$=32 mm of the projection edge were mirrored horizontally across the two truncation boundaries $r_+$ and $r_-$, and vertically across the respective lines equal to the value of the projection at each edge. The mirror images were then multiplied by the respective functions $c_+$ and $c_-$ as given by:

$$c_\pm(r) = \cos^2\left[\frac{\pi}{2w_2}(\pm r \mp r_\pm)\right] \quad \text{(Equation 11)}$$

where $w_2$ was set equal to 128 mm.

Figure 10:
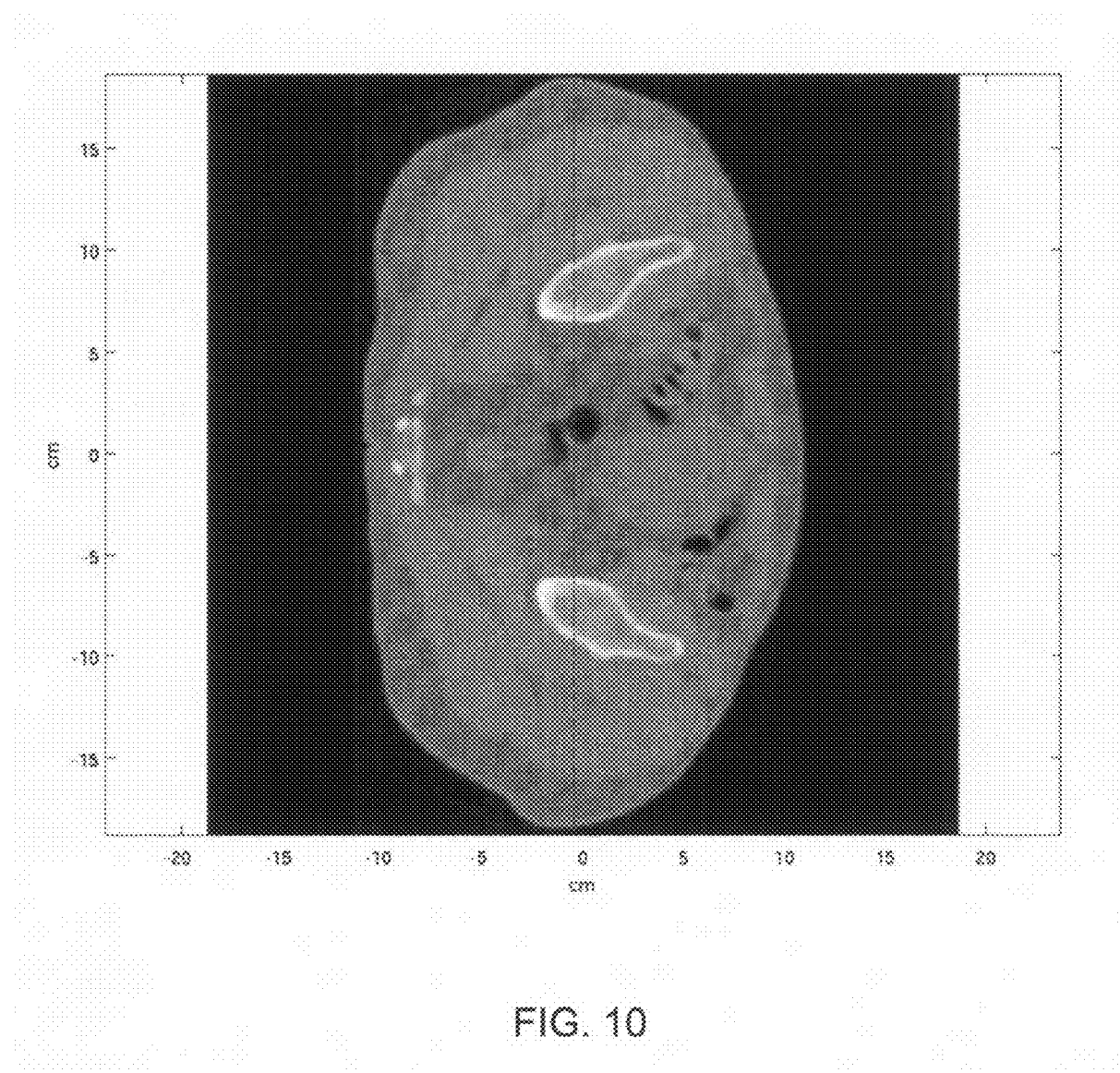
FIG. 10 depicts a complete representation of the complete original scan data.
Figure 11:
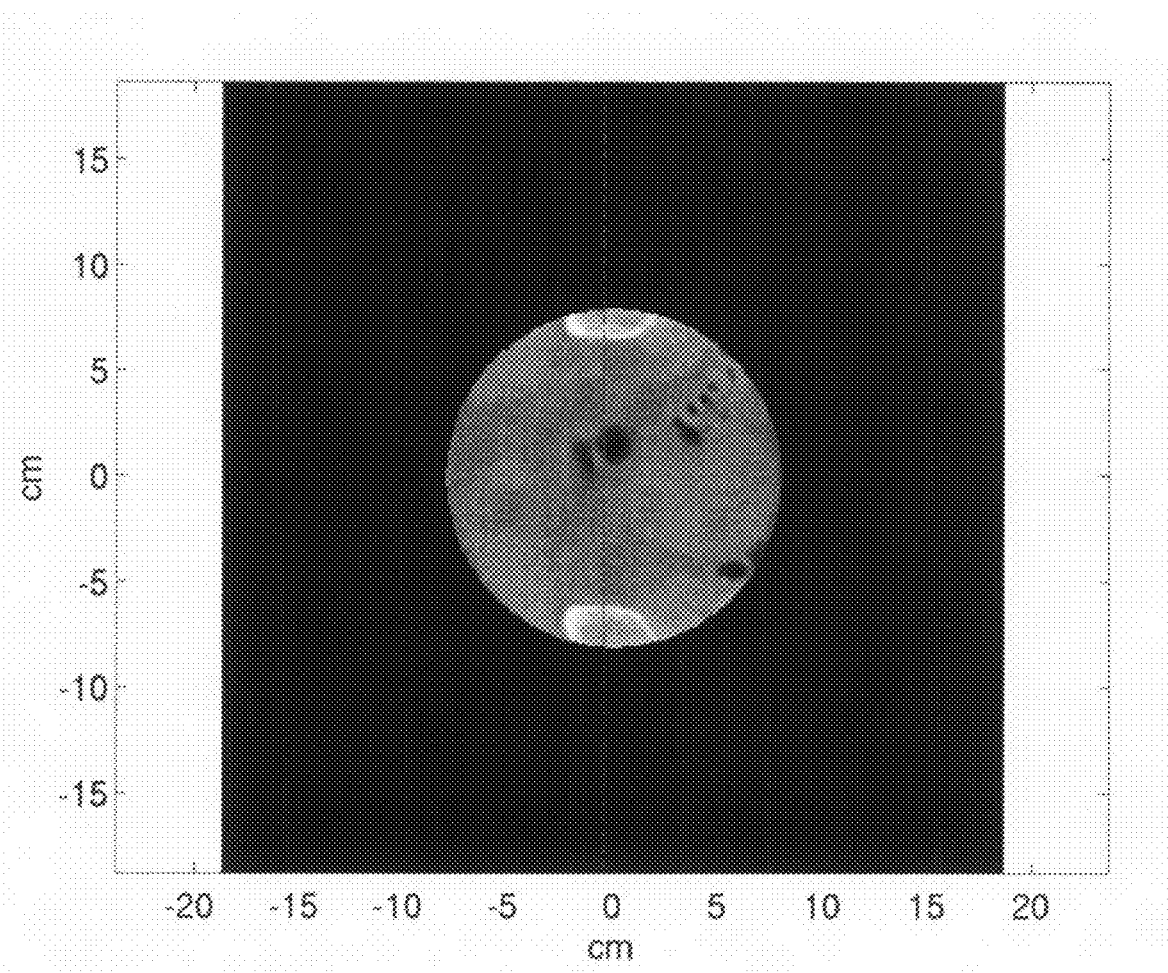
FIG. 11 depicts a reconstruction from empirically corrected truncated data.
Figure 12:
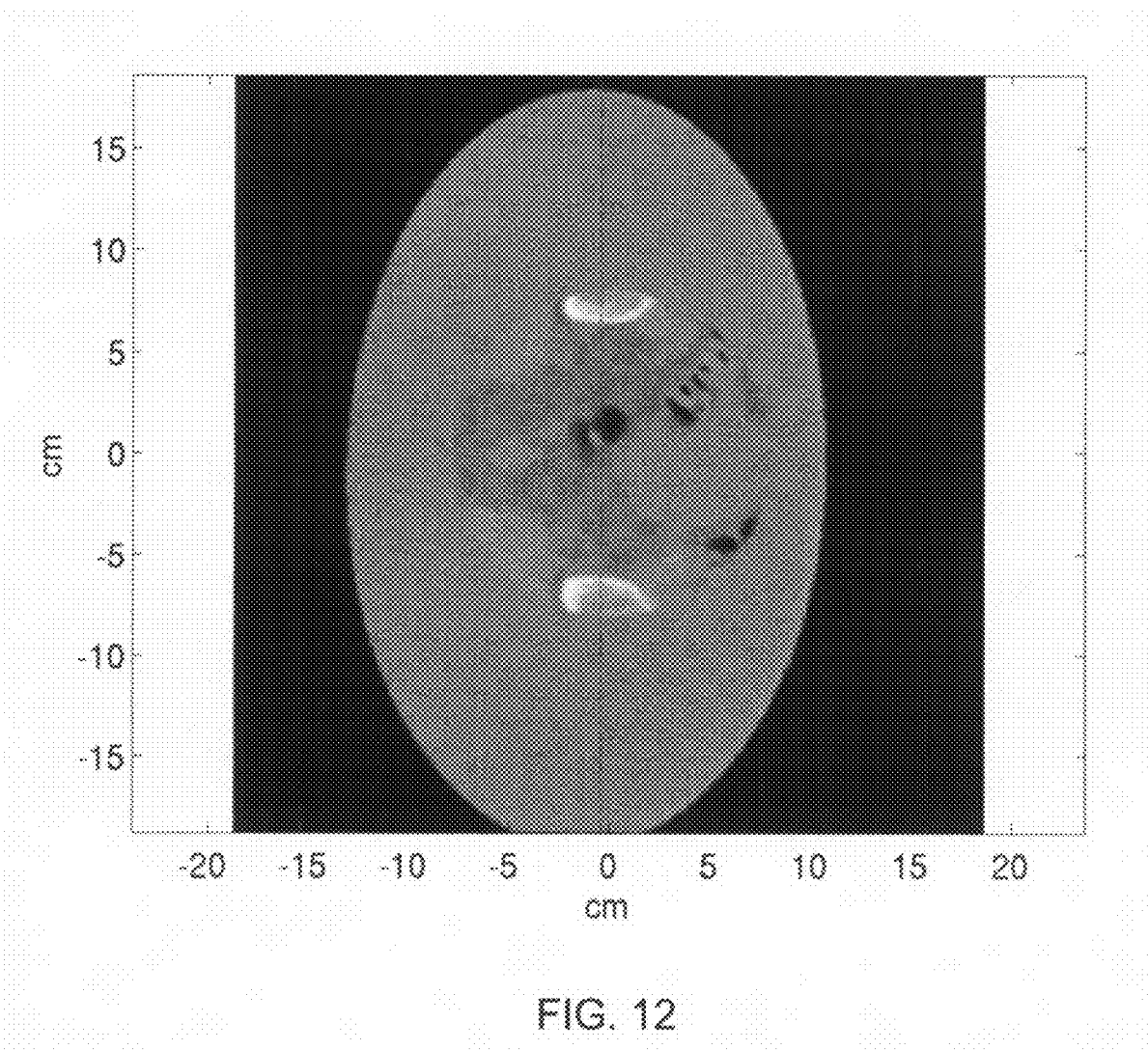
FIG. 12 depicts a reconstruction from data corrected according to the present invention.
Figure 13:
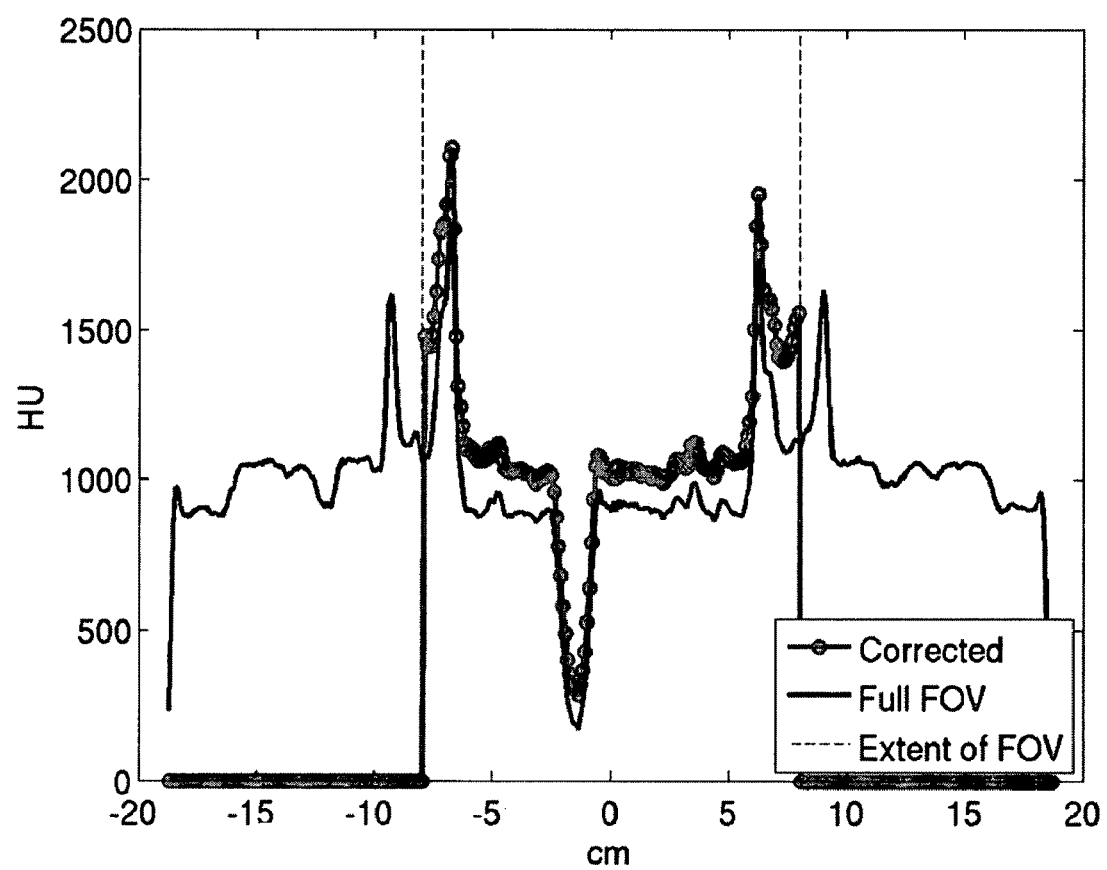
FIG. 13 depicts the vertical profile of the original scan data as compared to the reconstruction obtained after empirical truncation correction using the symmetric mirroring approach.
Figure 14:
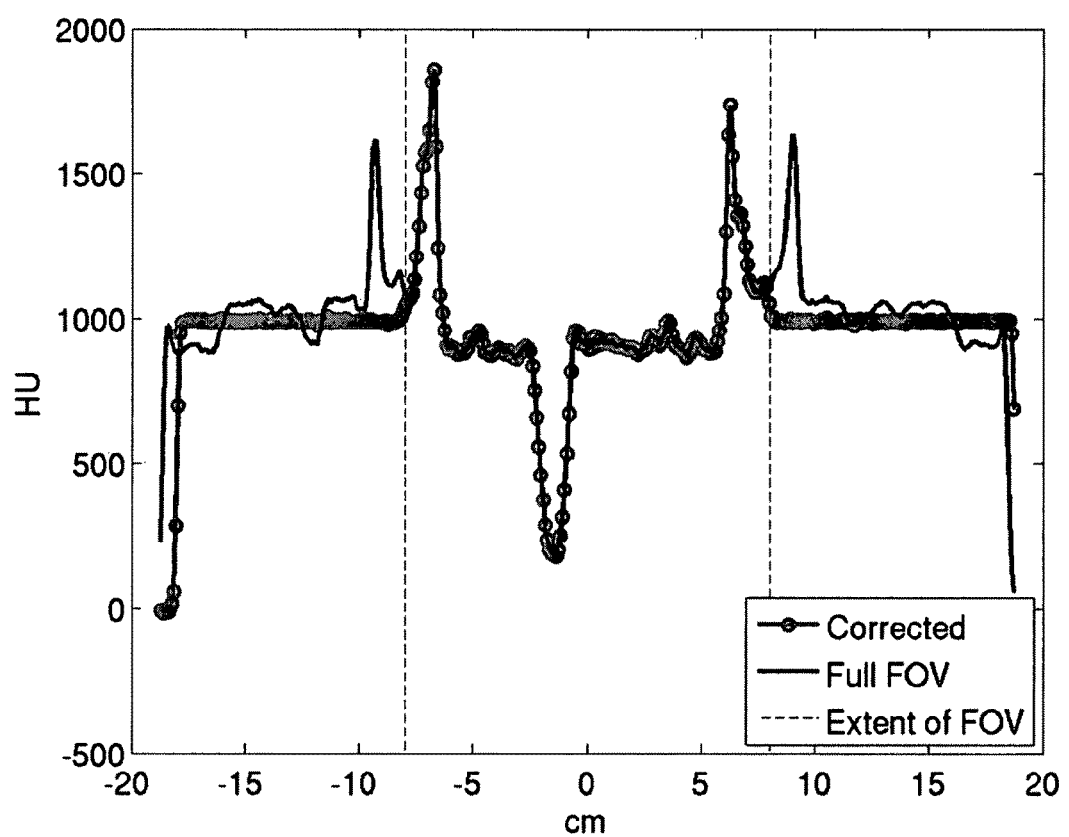
FIG. 14 depicts the vertical profile of the original scan data as compared to the corrected reconstructions.
Figure 15:
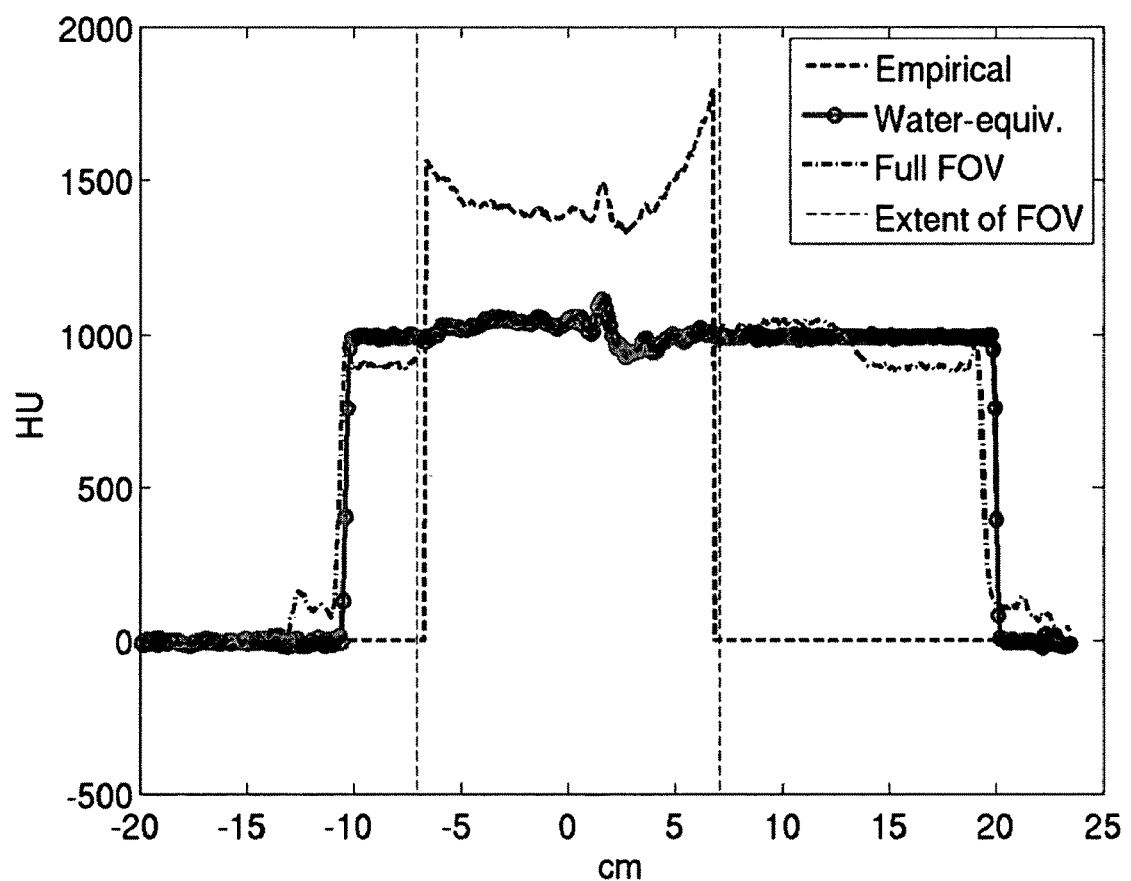
FIG. 15 depicts vertical profiles for a shifted-patient case.

Referring to FIGS. 10-12, images of: a) a reconstruction from empirically corrected truncated data; b) a reconstruction from data corrected according to the described methods; and c) a complete representation of the original scan data are presented, respectively. Referring to FIG. 13, the vertical profile of the original scan data (FIG. 10) is compared to the vertical profile of the empirically corrected reconstruction (FIG. 11) along a common axis (dotted line of FIGS. 10-11). Referring to FIG. 14, the vertical profile of the original scan data (FIG. 10) is compared to the vertical profile of the reconstruction corrected pursuant to the described methods (FIG. 12) along a common axis (dotted line of FIGS. 10 and 12). Analogous vertical profiles are shown for a shifted-patient case in FIG. 15 providing relative comparisons of the empirical reconstruction approach and the described reconstruction method when the center of the FOV is displaced from the centroid of the imaged object.

The RMS error as a percentage of the RMS of the reconstruction (within the FOV) is 20.4% for the uncorrected reconstruction and 1.0% for the reconstruction according to the described methods. For the shifted CT data (corresponding to a patient centered >10 cm from the isocenter), the uncorrected and corrected values are 56.2% and 4.4% respectively.

As such, the application of the described methodology may lead to improvements in the quantitative accuracy of CT images reconstructed from truncated projections. It may also be robust with respect to the presence of intervening physiological elements (such as bone which may bias thickness values) and against large shifts (>10 cm) of the patient centroid.

The error amplitude of the corrected reconstructions images is approximately 10 HU. As such, such images are thus sufficiently accurate for use in situ dose recalculation and dose reconstruction applications.

Figure 16:
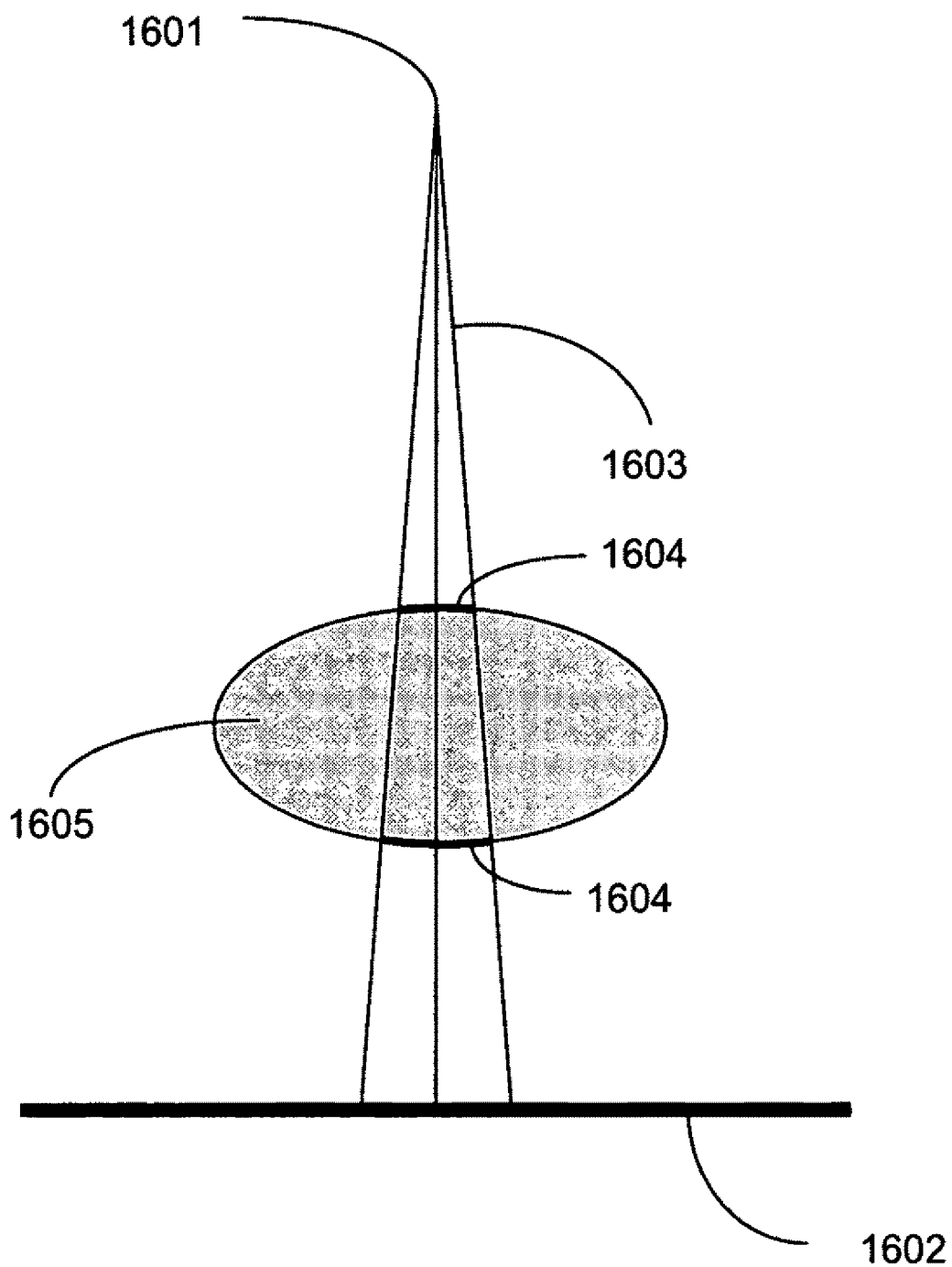
FIG. 16 depicts an application of a particular imaging geometry in which a cone or fan beam imaging source is employed.

Furthermore, it should be noted that it will be apparent to one skilled in the art that the above analysis is sufficiently general to accommodate any source geometry. For example, FIG. 16 shows an application of an imaging geometry in which a cone or fan beam imaging source 1601 is employed in conjunction with a large area flat panel detector 1602. In this example, three rays 1603 per projection may be employed, separated by 4.5 cm. These rays impinge on the central row of the detector 1602 (the row parallel to the transaxial slice at the isocenter). The rays are used to find the external contour 1604 of the imaged object 1605 at this slice. In this example, this contour is an ellipse and it is used to approximate the contours for all transaxial slices.

Figures 17A, 17B:
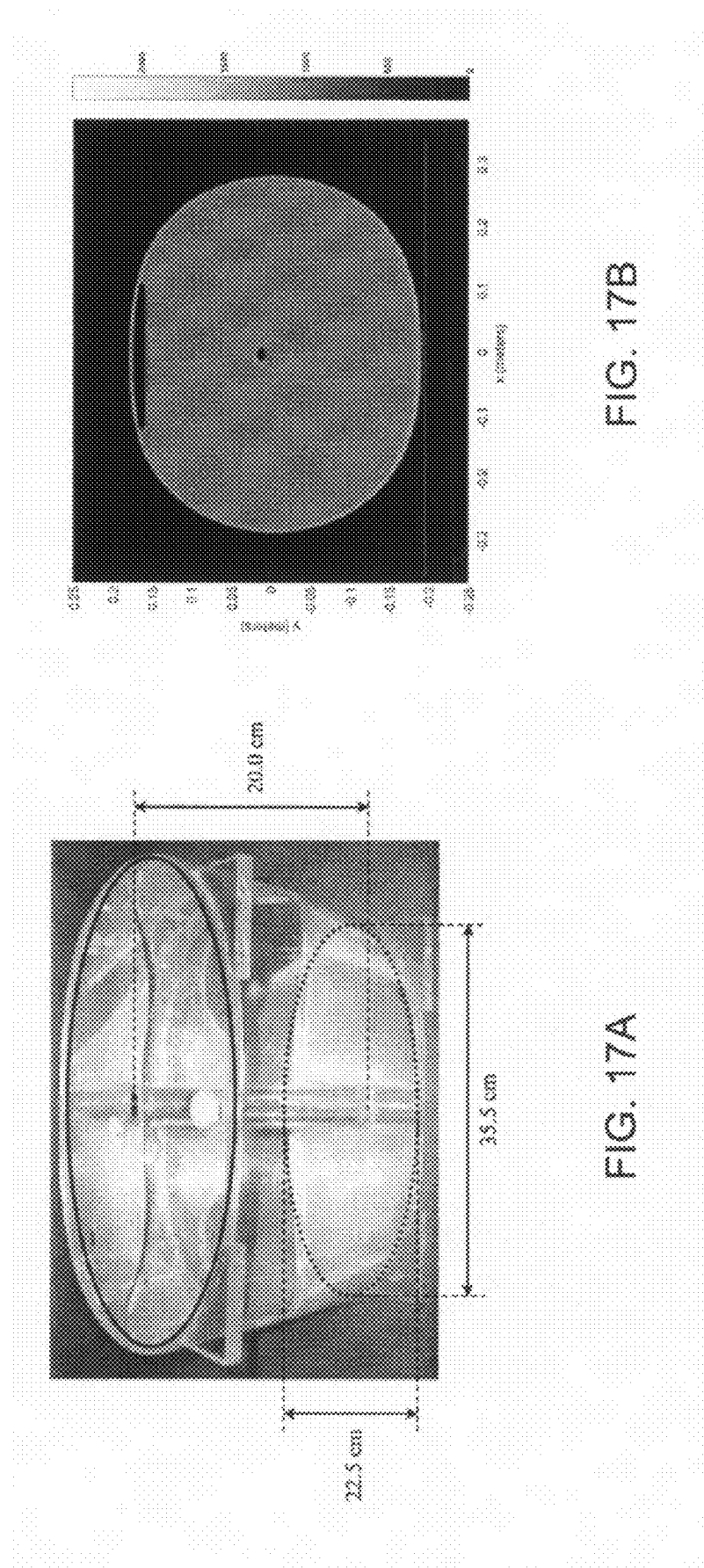
FIG. 17A depicts a water phantom.
FIG. 17B depicts a CT reconstruction of the water phantom obtained using a full field-of-view multi-slice CT system.
Figure 18A:
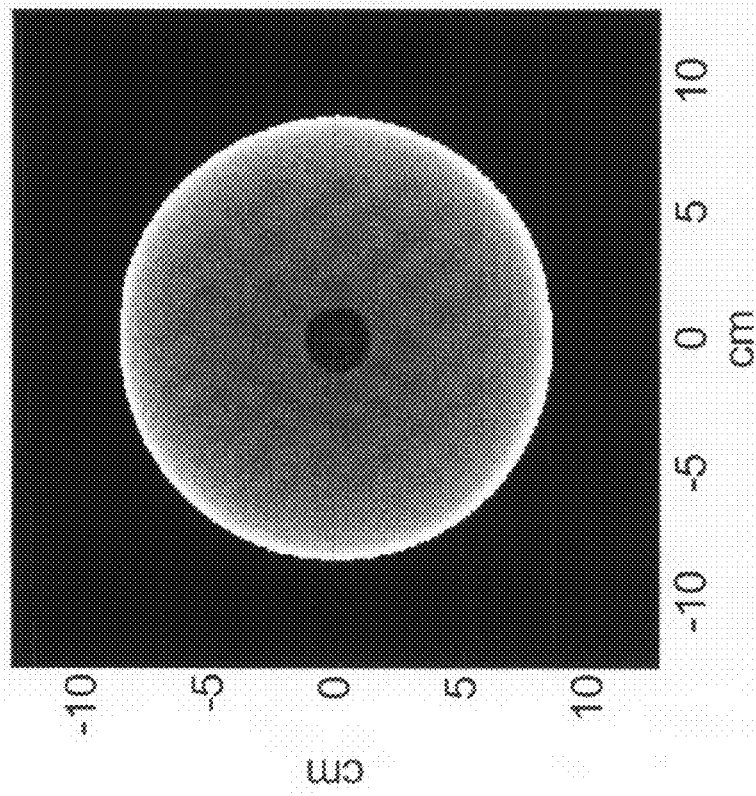
FIG. 18A depicts a CT reconstruction of the water phantom obtained using a cone beam CT imaging system having truncated portions.
Figure 18B:
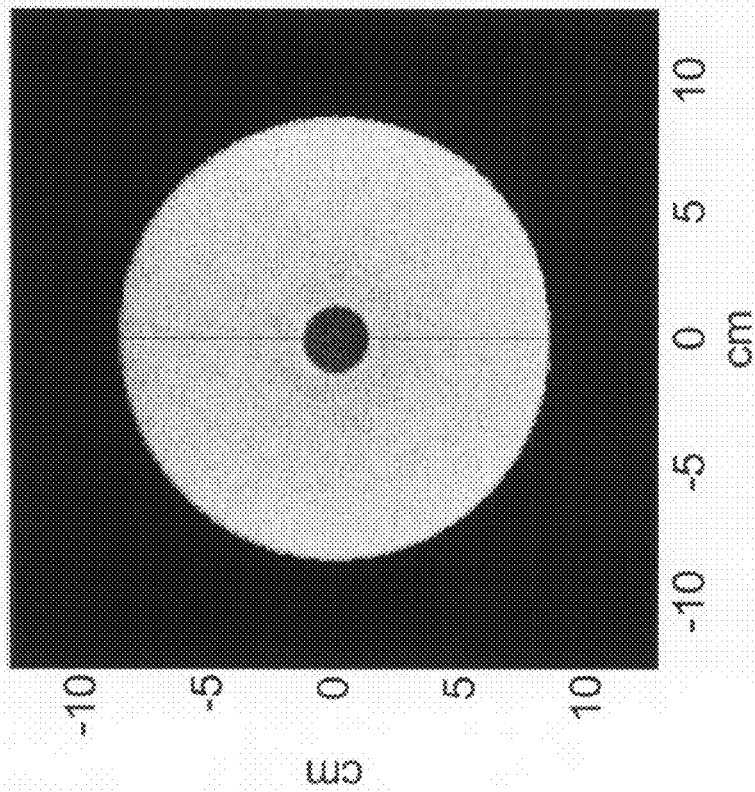
FIG. 18B depicts a CT reconstruction of the water phantom obtained using a cone beam CT imaging system where the truncated projections have been corrected using symmetric mirroring correction and the sampling geometry of FIG. 16.
Figure 19:
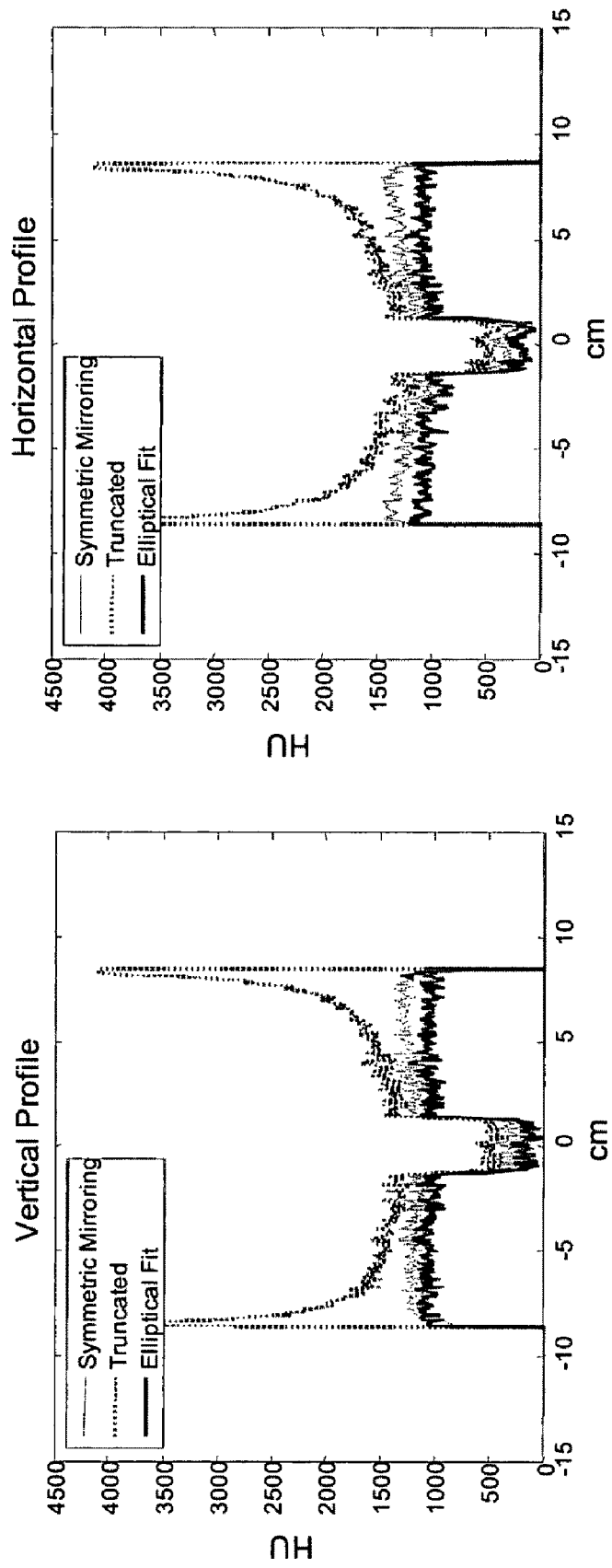
FIG. 19 depicts the horizontal and vertical profiles of a truncated reconstruction of the water phantom, a reconstruction corrected by symmetric-mirroring and a reconstruction corrected according to the present invention.

FIG. 17A shows a 35.5×22.5 cm water phantom. FIG. 17B depicts a CT reconstruction of the water phantom obtained using a full field-of-view multi-slice CT system. FIG. 18A depicts a CT reconstruction of the water phantom obtained using a cone beam CT imaging system having truncated projections that have not been corrected. FIG. 18B depicts a CT reconstruction of the water phantom obtained using a cone beam CT imaging system where the truncated projections have been corrected using symmetric mirroring correction and the sampling geometry of FIG. 16. FIG. 18C depicts a CT reconstruction of the water phantom obtained using a cone beam CT imaging system where the truncated projections have been corrected using the present algorithm and the sampling geometry of FIG. 16. FIG. 19 depicts the horizontal and vertical profiles of the truncated reconstruction of the water phantom, the reconstruction corrected by symmetric-mirroring and the reconstruction corrected according to the present invention.

One skilled in the art will recognize that the foregoing components (e.g., steps), devices, and objects in FIGS. 1-4 and the discussion accompanying them are used as examples for the sake of conceptual clarity and that various configuration modifications are common. Consequently, as used herein, the specific exemplars set forth in FIGS. 1-4 and the accompanying discussion are intended to be representative of their more general classes. In general, use of any specific exemplar herein is also intended to be representative of its class, and the non-inclusion of such specific components (e.g., steps), devices, and objects herein, or the order in which they are presented should not be taken as indicating that limitation is desired.

It is believed that the CT imaging system and method and many of their attendant advantages will be understood from the foregoing description, and it will be apparent that various changes may be made in the form, construction, and arrangement of the components thereof without departing from the scope and spirit of the described CT imaging system and method or without sacrificing all of their material advantages. The form herein before described being merely an explanatory embodiment thereof, it is the intention of the following claims to encompass and include such changes.

What is claimed is:

1. A method for computed tomography (CT) imaging, the method comprising the steps:
   obtaining CT projections of an object, the projections comprising at least one truncated projection;
   calculating material-equivalent thickness (MET) values for the truncated projection;
   establishing parameterized point-pairs separated in distance by the MET values;
   fitting the parameterized point-pairs to a parameterized curve or to a set of curves according to a set of constraints on spatial relationships between the point-pairs;
   completing the truncated projection; and
   reconstructing a CT image from non-truncated projections and the completed truncated projection.

2. The method of claim 1,
wherein the step of calculating the MET values for the truncated projection comprises the steps:
   fitting a primary transmission model for propagation through a material having a composition analogous to that of the object to a resultant imaging beam; and
   converting measured x-ray transform values into a MET value.

3. The method of claim 1,
wherein the step of calculating the MET values for the truncated projection comprises the step:
   obtaining fan or cone beam computed tomography projections.

4. The method of claim 1,
further comprising the step:
   correcting MET values for anomalous portions of the object.

5. The method of claim 4,
wherein the step of correcting MET values further comprises the step:
   modifying a sinogram by replacing a first ray sample with a second ray sample;
   reconstructing the modified sinogram.

6. The method of claim 4,
wherein the step of correcting MET values further comprises the step:
   substituting an air volume thickness for the MET.

7. The method of claim 1,
wherein the parameterized curve is an ellipse.

8. The method of claim 1,
wherein the step of fitting the parameterized point-pairs to a parameterized curve further comprises the step:
   calculating a metric correlating the goodness-of-fit between the parameterized point-pairs and the parameterized curve.

9. The method of claim 8,
wherein the metric is the squared norm of a vector of plurality of vectors,
wherein the vector of the plurality of vectors joins a point of a parameterized point-pair to the parameterized curve,
wherein the vector of the plurality of vectors intersects the centroid of the parameterized curve.

10. The method of claim 9, further comprising the step:
   minimizing a sum of the squared norms the plurality of the vectors.

11. A non-transitory computer readable storage medium having computer readable instructions for carrying out a method for computed tomography (CT) imaging, the method comprising the steps:
   obtaining CT projections of an object, the projections comprising at least one truncated projection;
   calculating material-equivalent thickness (MET) values for the truncated projection;
   establishing parameterized point-pairs separated in distance by the MET values;
   fitting the parameterized point-pairs to a parameterized curve or to a set of curves according to a set of constraints on spatial relationships between the point-pairs;
   completing the truncated projection; and reconstructing a CT image from non-truncated projections and the completed truncated projection.

12. The computer readable storage medium of claim 11, wherein the step of calculating the MET values for the truncated projection comprises the steps:
   fitting a primary transmission model for propagation through a material having a composition analogous to that of the object to the resultant imaging beam; and
   converting measured x-ray transform values into METs.

13. The computer readable storage medium of claim 11, wherein the step of calculating the MET values for the truncated projection comprises the step:
   obtaining fan or cone beam computed tomography projections.

14. The computer readable storage medium of claim 11, further comprising the step:
   correcting MET values for anomalous portions of the object.

15. The computer readable storage medium of claim 14, wherein the step of correcting MET values further comprises the step:
   modifying a sinogram by replacing a first ray sample with a second ray sample;
   reconstructing the modified sinogram.

16. The computer readable storage medium of claim 14, wherein the step of correcting MET values further comprises the step:
   substituting an air volume thickness for the MET.

17. The computer readable storage medium of claim 11, wherein the parameterized curve is an ellipse.

18. The computer readable storage medium of claim 11, wherein the step of fitting the parameterized point-pairs to a parameterized curve further comprises the step:
   calculating a metric correlating the goodness-of-fit between the parameterized point-pairs and the parameterized curve.

19. The computer readable storage medium of claim 11, wherein the metric is a squared norm of a vector of plurality of vectors,
   wherein the vector of the plurality of vectors joins a point of a parameterized point-pair to the parameterized curve,
   wherein the vector of the plurality of vectors intersects the centroid of the parameterized curve.

20. The computer readable storage medium of claim 11, further comprising the step:
   minimizing a sum of the squared norms the plurality of the vectors.

21. A system for CT imaging, the system comprising:
   an x-ray source;
   an x-ray detector; and
   a processing unit,
   wherein the processing unit is configured to carry out the steps:
      obtaining CT projections of an object, the projections comprising at least one truncated projection;
      calculating material-equivalent thickness (MET) values for the truncated projection;
      establishing parameterized point-pairs separated in distance by the MET values;
      fitting the parameterized point-pairs to a parameterized curve or to a set of curves according to a set of constraints on spatial relationships between the point-pairs;
      completing the truncated projection; and
      reconstructing a CT image from non-truncated projections and the completed truncated projection.

22. The system of claim 21, further comprising the step:
   correcting MET values for anomalous portions of the object.

23. The system of claim 22, wherein the step of correcting MET values further comprises the step:
   modifying a sinogram by replacing a first ray sample with a second ray sample;
   reconstructing the modified sinogram.

24. The system of claim 22, wherein the step of correcting MET values further comprises the step:
   substituting an air volume thickness for the MET.

* * * * *